United States Patent
Brumfield et al.

(10) Patent No.: US 11,583,321 B2
(45) Date of Patent: Feb. 21, 2023

(54) FACET SCREW SYSTEM AND METHOD

(71) Applicant: Amendia, Inc., Carlsbad, CA (US)

(72) Inventors: David Brumfield, Collierville, TN (US); Mahmoud Abdelgany, Rockaway, NJ (US); Ahmad Faizan, Rockaway, NJ (US); Faheem Sandhu, Washington, DC (US)

(73) Assignee: Spinal Elements, Inc., Carlsbad, CA (US)

( * ) Notice: Subject to any disclaimer, the term of this patent is extended or adjusted under 35 U.S.C. 154(b) by 444 days.

(21) Appl. No.: 16/395,709

(22) Filed: Apr. 26, 2019

(65) Prior Publication Data

US 2019/0247098 A1   Aug. 15, 2019

Related U.S. Application Data

(60) Continuation of application No. 15/614,054, filed on Jun. 5, 2017, now Pat. No. 10,314,622, which is a division of application No. 13/657,826, filed on Oct. 22, 2012, now Pat. No. 9,668,784.

(60) Provisional application No. 61/549,979, filed on Oct. 21, 2011.

(51) Int. Cl.
*A61B 17/70* (2006.01)
*A61B 17/88* (2006.01)
*A61B 90/00* (2016.01)

(52) U.S. Cl.
CPC ...... *A61B 17/7064* (2013.01); *A61B 17/8863* (2013.01); *A61B 2090/037* (2016.02)

(58) Field of Classification Search
CPC .................................................. A61B 17/7064
See application file for complete search history.

(56) References Cited

U.S. PATENT DOCUMENTS

| 519,411 | A | | 5/1894 | North | |
|---|---|---|---|---|---|
| 5,352,231 | A | * | 10/1994 | Brumfield | A61B 17/7091 606/99 |
| 5,439,005 | A | * | 8/1995 | Vaughn | A61B 17/1633 279/42 |
| 5,613,968 | A | | 3/1997 | Lin | |
| 5,643,259 | A | | 7/1997 | Sasso et al. | |
| 5,645,546 | A | | 7/1997 | Fard | |
| 6,187,005 | B1 | | 2/2001 | Brace et al. | |
| 6,485,518 | B1 | | 11/2002 | Cornwall et al. | |
| 9,795,412 | B2 | | 10/2017 | Sinha | |
| 2003/0032960 | A1 | | 2/2003 | Dudasik | |
| 2003/0149436 | A1 | | 8/2003 | McDowell | |
| 2004/0267275 | A1 | | 12/2004 | Cournoyer et al. | |
| 2005/0033289 | A1 | * | 2/2005 | Warren | A61B 17/746 606/53 |
| 2005/0131545 | A1 | | 6/2005 | Chervitz et al. | |
| 2005/0277923 | A1 | | 12/2005 | Sweeney | |
| 2006/0200149 | A1 | * | 9/2006 | Hoy | A61B 17/7064 623/17.11 |
| 2006/0212034 | A1 | | 9/2006 | Triplett et al. | |

(Continued)

FOREIGN PATENT DOCUMENTS

WO          9702786          1/1997

*Primary Examiner* — Tessa M Matthews

(57) ABSTRACT

A facet screw system and method includes an implant assembly having a screw with a removable head, a locking nut, and a collet. An insertion instrument is used to insert the screw, compress the facet joint, locks the implant, and breaks off the head of the screw providing a lower profile implant.

15 Claims, 9 Drawing Sheets

(56) References Cited

U.S. PATENT DOCUMENTS

| | | |
|---|---|---|
| 2007/0123860 A1 | 5/2007 | Francis |
| 2007/0270859 A1 | 11/2007 | Companioni et al. |
| 2008/0021480 A1 | 1/2008 | Chin et al. |
| 2009/0092462 A1 | 4/2009 | Pratt |
| 2009/0131986 A1 | 5/2009 | Lee |
| 2009/0192551 A1 | 7/2009 | Cianfrani |
| 2009/0248089 A1 | 10/2009 | Jacofsky |
| 2009/0312763 A1 | 12/2009 | McCormack |
| 2010/0114170 A1 | 5/2010 | Barrus et al. |
| 2010/0198272 A1 | 8/2010 | Keyer et al. |
| 2010/0249846 A1 | 9/2010 | Simonson |
| 2010/0298838 A1 | 11/2010 | Walters |
| 2011/0313472 A1 | 12/2011 | Yap |
| 2012/0022603 A1 | 1/2012 | Kirschman |
| 2012/0116454 A1 | 5/2012 | Edidin |
| 2012/0116732 A1 | 5/2012 | Barnes et al. |
| 2012/0186993 A1 | 7/2012 | Huang et al. |
| 2012/0226325 A1 | 9/2012 | Lyons |
| 2013/0226245 A1 | 8/2013 | Wallenstein et al. |
| 2014/0114418 A1 | 4/2014 | Landry |
| 2014/0288601 A1 | 9/2014 | Baynham |
| 2015/0142056 A1 | 5/2015 | Hart |
| 2017/0319241 A1 | 11/2017 | Fauth |

\* cited by examiner

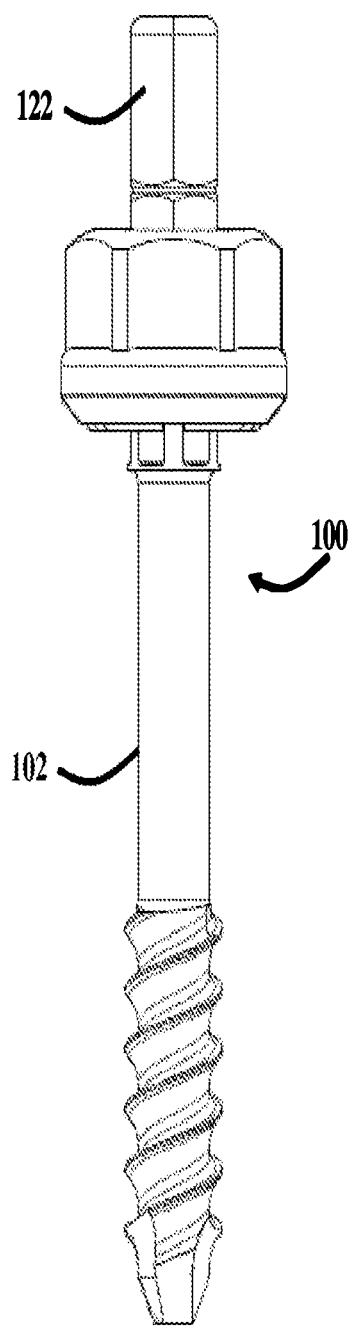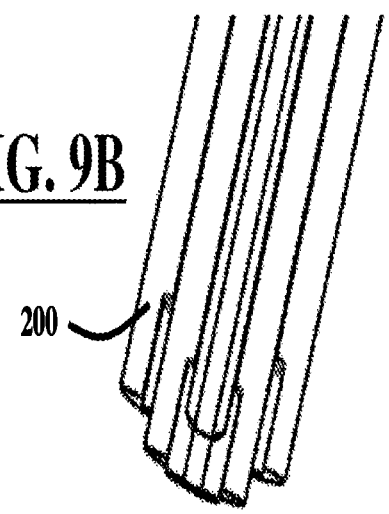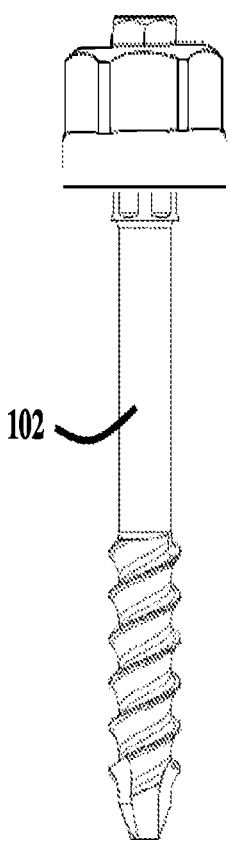

FACET SCREW SYSTEM AND METHOD

CROSS-REFERENCE TO RELATED APPLICATIONS

This application is a continuation of U.S. application Ser. No. 15/614,054 filed Jun. 5, 2017, which is a division of U.S. application Ser. No. 13/657,826 filed Oct. 22, 2012, now U.S. Pat. No. 9,668,784 issued Jun. 6, 2017, which claims the benefit of U.S. provisional application No. 61/549,979, filed on Oct. 21, 2011, the complete disclosures of each of which, in their entireties, are hereby incorporated by reference.

BACKGROUND

Technical Field

The embodiments herein generally relate to lumbar and cervical fusion devices, and, more particularly, to a facet screw system and method used in spinal surgeries.

Description of the Related Art

Conventional lumbar fusion, facet screws, facet fusion, and screw fixation systems include devices described in U.S. Pat. No. 6,485,518, U.S. Patent Publication No. 2005/0149030, and U.S. Patent Publication No. 2009/0192551, the complete disclosures of which, in their entireties, are herein incorporated by reference.

SUMMARY

In view of the foregoing, an embodiment herein provides a novel screw mechanism that is used to immobilize the facet joint in order to facilitate fusion in the human spine. The embodiments herein allow an infinite degree of compression after the screw is fully inserted, which provides superior net fixation than fixed-head devices which allow compression only by continued screw insertion after the screw head abuts the cortical surface of the bone. The embodiments herein provide an instrument which sequentially inserts the screw, compresses the facet joint, and locks the system in place, with all of the steps performed with only one implant/instrument engagement.

One embodiment provides a medical implant assembly comprising a bone securing component comprising a first part and a second part; a locking mechanism positioned around the second part of the bone securing component; and a holding mechanism positioned through the locking mechanism and around the second part of the bone securing component. The bone securing component may comprise a screw mechanism adapted to be inserted into the bone. The locking mechanism may comprise a locking nut comprising a first set of threads. The holding mechanism may comprise a collet comprising a plurality of flexible flanges arranged in a substantially radial configuration; a second set of threads that are configured to mate with the first set of threads of the locking nut; and a hole configured through a center of the collet. In one embodiment, each of the plurality of flexible flanges comprises an outwardly protruding end positioned at an end of the collet opposite to the second set of threads. The first part of the bone securing component may be adapted to break off from the second part after insertion of the bone securing component into bone.

Another embodiment provides a medical apparatus used on a facet joint in a body, the apparatus comprising a bone securing component that engages the facet joint; a locking mechanism positioned around the bone securing component; a holding mechanism positioned through the locking mechanism and around the bone securing component; and an insertion tool configured to attach to the holding mechanism. The bone securing component may comprise a screw mechanism adapted to be inserted into a bone of the facet joint. The locking mechanism may comprise a locking nut comprising a first set of threads. The holding mechanism may comprise a collet comprising a plurality of flexible flanges arranged in a substantially radial configuration; a second set of threads that are configured to mate with the first set of threads of the locking nut; and a hole configured through a center of the collet. Each of the plurality of flexible flanges may comprise an outwardly protruding end positioned at an end of the collet opposite to the second set of threads. The insertion tool may comprise a shaft that engages the bone securing component wherein rotation of the shaft causes rotation of the bone securing component, and wherein rotation of the bone securing component causes insertion of the bone securing component into the bone. The insertion tool may comprise means for applying compression on the facet joint. The bone securing component may comprise a first part and a second part, wherein the first part is adapted to break off from the second part after insertion of the bone securing component into a bone of the facet joint. The insertion tool locks the holding mechanism onto the locking mechanism by inwardly forcing the plurality of flanges of the collet against the bone securing component. Moreover, the insertion tool also serves to allow the engagement and tightening of the locking mechanism with the holding mechanism, which inwardly forces the plurality of flanges of the collet against the bone securing component.

Another embodiment provides a method of compressing a facet joint in a body, the method comprising inserting a medical implant into a bone in the facet joint by rotating an insertion tool that holds the medical implant, wherein the medical implant comprises a bone securing component, a locking mechanism positioned around the bone securing component, and a holding mechanism positioned around the bone securing component and through the locking mechanism; compressing the facet joint by pressing the insertion tool and the medical implant against the facet joint; and locking the locking mechanism and the holding mechanism around the bone securing component. The method may further comprise breaking off a top part of the medical implant. The locking mechanism may comprise a locking nut comprising a first set of threads. The holding mechanism may comprise a collet comprising a plurality of flexible flanges arranged in a substantially radial configuration; a second set of threads that are configured to mate with the first set of threads of the locking nut; and a hole configured through a center of the collet. Each of the plurality of flexible flanges may comprise an outwardly protruding end positioned at an end of the collet opposite to the second set of threads. The insertion tool may comprise a shaft that engages the bone securing component, wherein rotation of the shaft causes rotation of the bone securing component, and wherein rotation of the bone securing component causes insertion of the bone securing component into the bone.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIGS. 9A through 9C are schematic diagrams illustrating a break off process according to an embodiment herein.

DETAILED DESCRIPTION OF PREFERRED EMBODIMENTS

Figure 1:
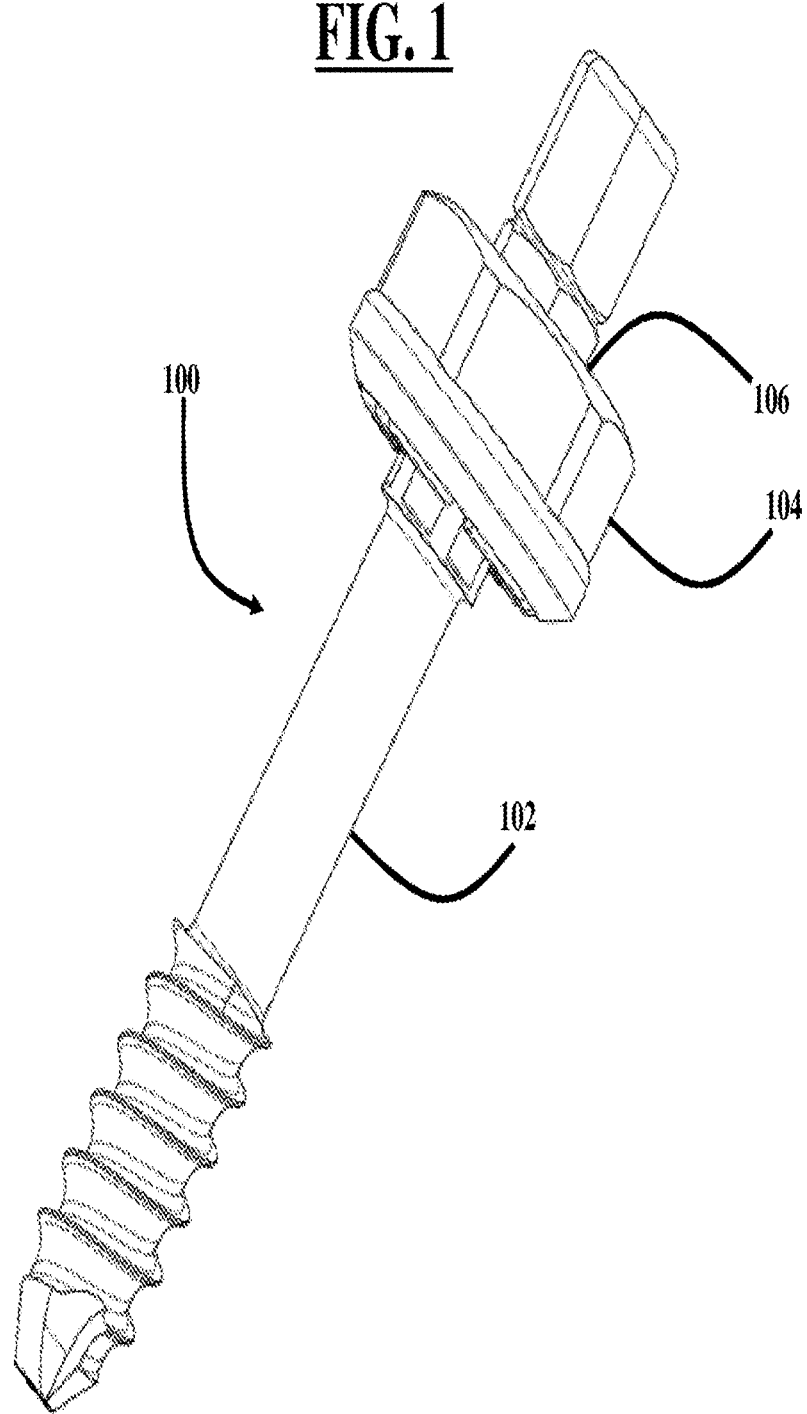
FIG. 1 illustrates a schematic diagram of an implant assembly according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein provide a facet screw system and method that include an implant assembly having a screw with a removable head, a locking nut, and a collet. An insertion instrument is used to insert the screw, compress the facet joint, locks the implant, and breaks off the head of the screw providing a lower profile implant. Referring now to the drawings, and more particularly to FIGS. 1 through 9C, where similar reference characters denote corresponding features consistently throughout the figures, there are shown preferred embodiments.

Lumbar spine fusion using pedicle screws and rods is a widely popular procedure in spinal surgeries. The pedicle screws and rods construct immobilizes the spinal segment and hence facilitates fusion. Facet screws are an alternative method of immobilizing the spinal segment. The embodiments herein provide a system and method of immobilizing the facet joint. The device is inserted through the facet joint and then it is used to apply compression to the facet joint. Finally, the device is locked in place. Hence, the device immobilizes the facet joint and enhances fusion in the spine. The device may be used to immobilize the facet joint or it may be used to fix any other two bones.

FIG. 1 illustrates a schematic diagram of an implant assembly 100 according to an embodiment herein. The assembly 100 includes a screw 102, a locking nut 104 positioned around the screw 102, and a collet 106 positioned through the locking nut 104 and around the screw 102.

Figure 2:
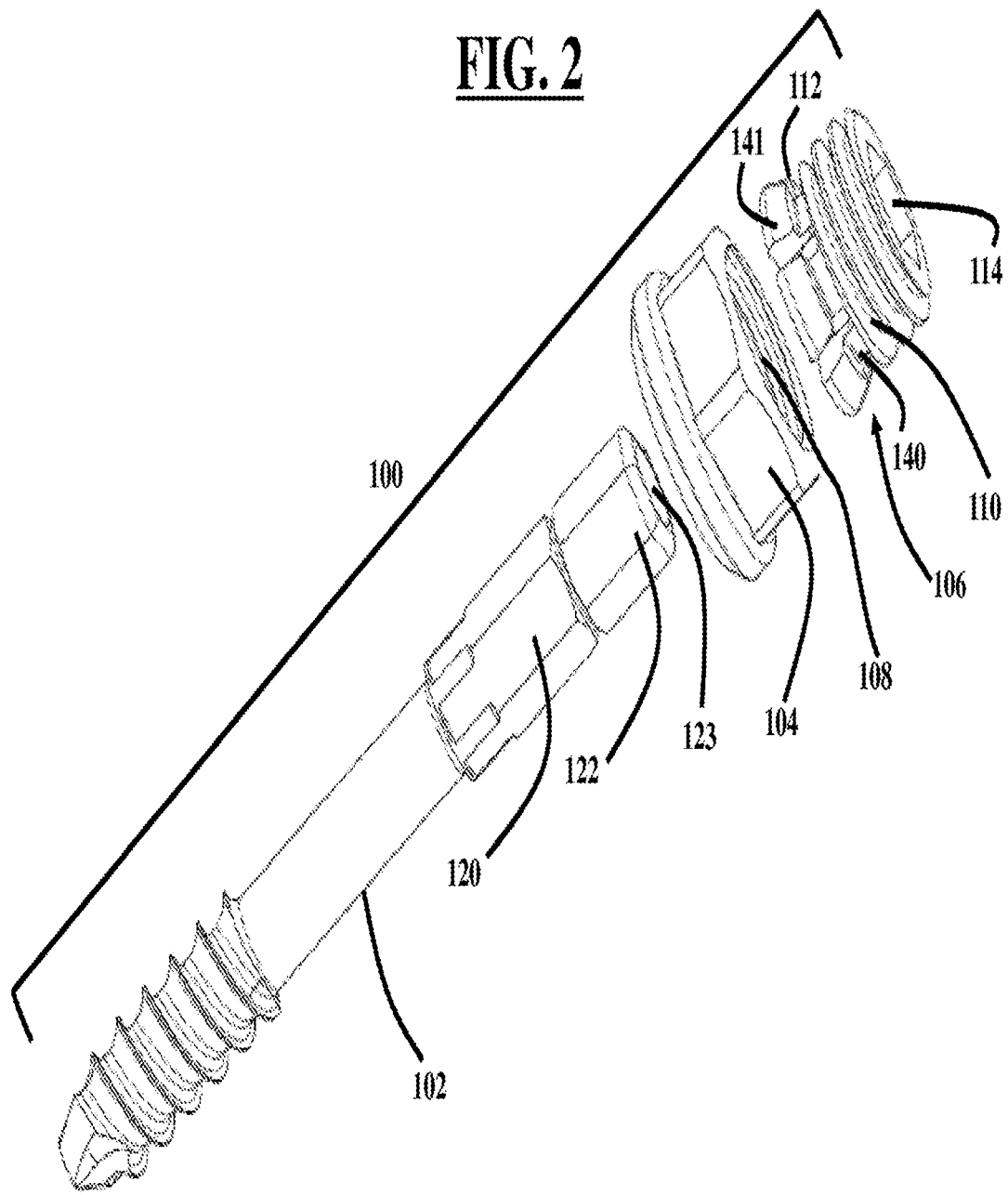
FIG. 2 illustrates an exploded view of an implant assembly according to an embodiment herein.

FIG. 2, with reference to FIG. 1, illustrates an exploded view of an implant assembly 100 according to an embodiment herein. In this view the threads 108 of the locking nut 104 are visible. The threads 108 of the locking nut 104 engage the corresponding mating threads 110 of the collet 106 upon insertion of the collet 106 into the locking nut 104. The collet 106 includes a plurality of flexible flanges 112 configured in a substantially radial configuration such that the overall configuration of the collet 106 is substantially cylindrical and, in one embodiment, is hollow. The collet 106 further includes a hole 114 or other means dimensioned and configured to receive the neck portion 120 of screw 102.

Figure 3A:
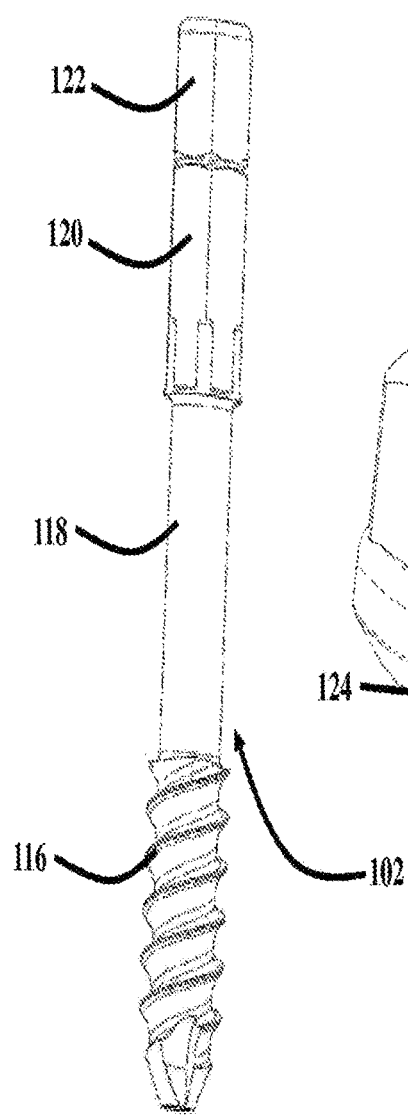
FIG. 3A illustrates a schematic diagram of the screw of an implant assembly according to an embodiment herein.

FIG. 3A, with reference to FIGS. 1 through 2, illustrates a schematic diagram of the screw 102 of an implant assembly 100 according to an embodiment herein. The screw 102 includes a threaded portion 116, which is dimensioned and configured to be able to anchor into bone 400 (of FIGS. 6B and 6C). A substantially cylindrical central shaft 118 is positioned on top of the threaded portion 116. A neck portion 120 is positioned on top of the shaft 118, and a head 122 is positioned on top of the neck portion 120. In one embodiment, the neck portion 120 and head 122 are hex-shaped.

Figure 3B:
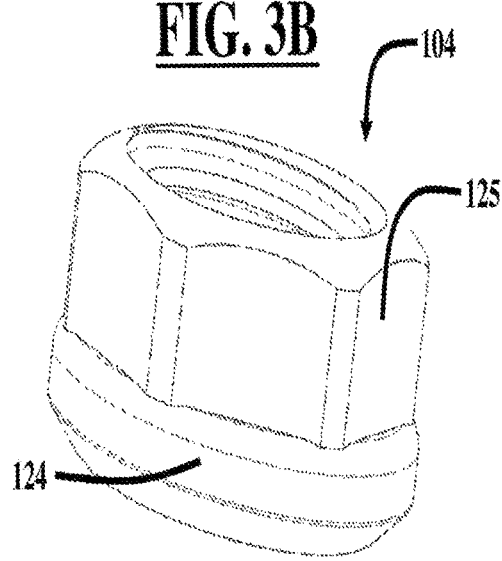
FIG. 3B illustrates a schematic diagram of the locking nut of an implant assembly according to an embodiment herein.

FIG. 3B, with reference to FIGS. 1 through 3A, illustrates a schematic diagram of the locking nut 104 of an implant assembly 100 according to an embodiment herein. The outer walls 125, which may be angled (e.g., in a hex configuration, for example), of the locking nut 104 are dimensioned and configured to be able to be gripped by an insertion tool. A bottom lip 124 is circumferentially disposed around the lower portion of the locking nut 104.

Figure 3C:
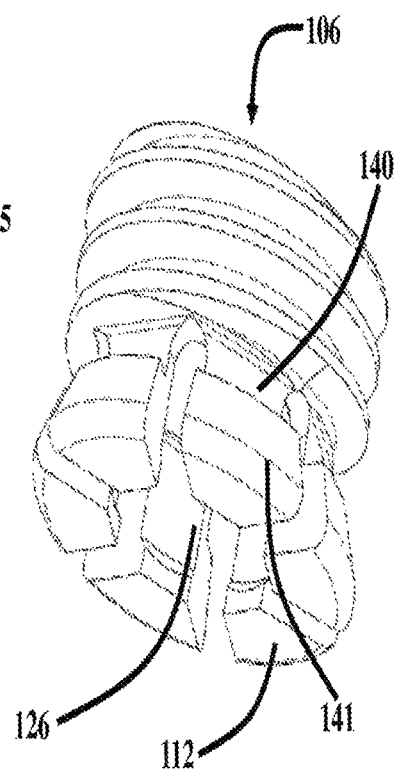
FIG. 3C illustrates a schematic diagram of the collet of an implant assembly according to an embodiment herein.

FIG. 3C, with reference to FIGS. 1 through 3B, illustrates a schematic diagram of the collet 106 of an implant assembly 100 according to an embodiment herein. The collet 106 also includes a central hole 126 configured inside the radial configuration of the flanges 112. In one embodiment, the collet 106 is configured having threads 110 which may be optionally left-handed to engage with complementary threads of locking nut 104 to tighten the collet 106 onto the neck portion 120 of screw 102, allow for breakoff of head 122 of screw 102, and permit easy removal of the assembly 100 after insertion, if necessary. The collet 106 may be configured as any suitable type of holding mechanism, chuck, or collar device that provides for easy removal of the assembly 100 after insertion, if necessary. In one embodiment, each of the flanges 112 comprise a flat wall 140 adjacent to the threads 110, and a protruding end 141 attached to the flat wall 140 such that the protruding end 141 which outwardly protrude and extend beyond the plane defined by the flat wall 140.

Figure 4:
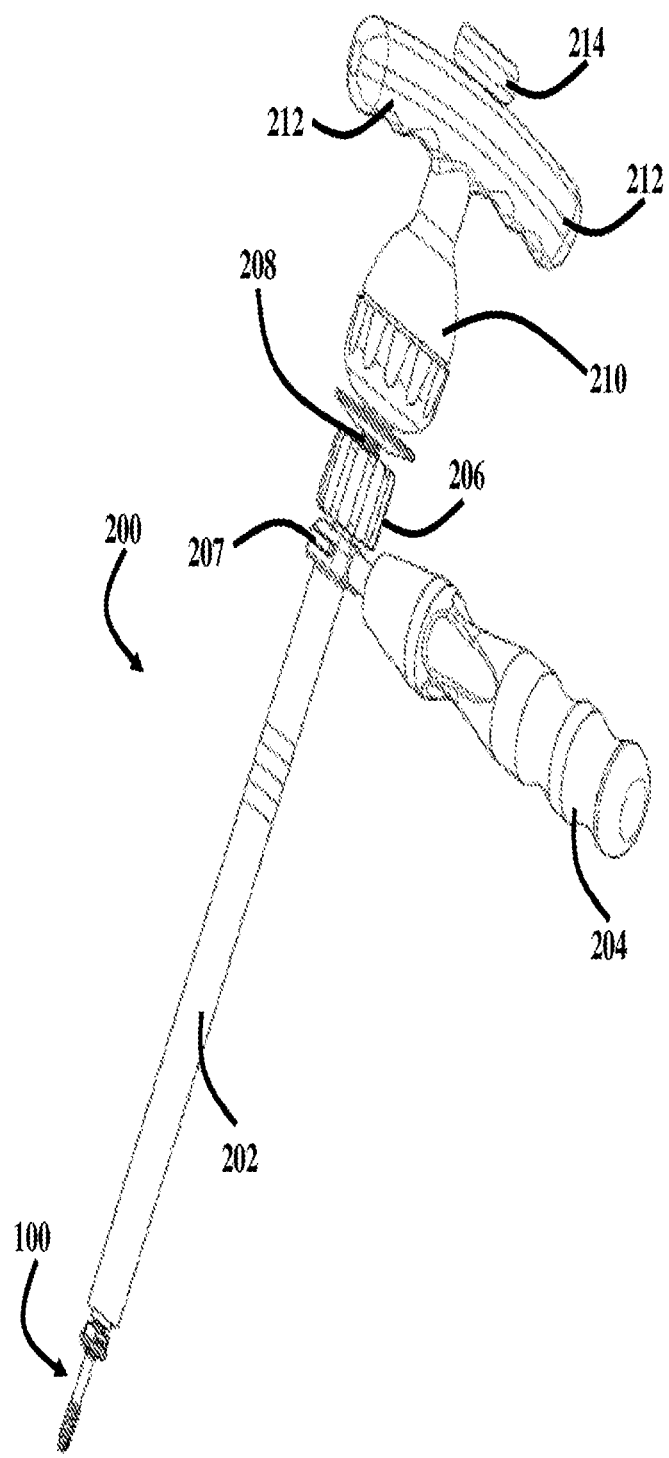
FIG. 4 illustrates a schematic diagram of an implant assembly in combination with an insertion instrument according to an embodiment herein.

FIG. 4, with reference to FIGS. 1 through 3C, illustrates a schematic diagram of an implant assembly 100 in combination with an insertion instrument 200 according to an embodiment herein. The insertion instrument 200 includes an engaging shaft 202, which may be hollow. A locking handle 204 is operatively connected to the shaft 202. A button 207 is connected to the shaft 202, and may be configured near the connection of the locking handle 204 to the shaft 202, in one embodiment. A compression knob 206 connects above the shaft 202 and is disposed around a screwdriver 208. The screwdriver 208 may be positioned to extend through the shaft 202 to engage the assembly 100 and connects to a handle 210 having a pair of gripping arms 212 (e.g., arranged in a T-shape configuration). A stabilizer 214 is positioned through the screwdriver 208 and the shaft 202 and may be positioned above the handle 210 and arms 212.

Figure 5:
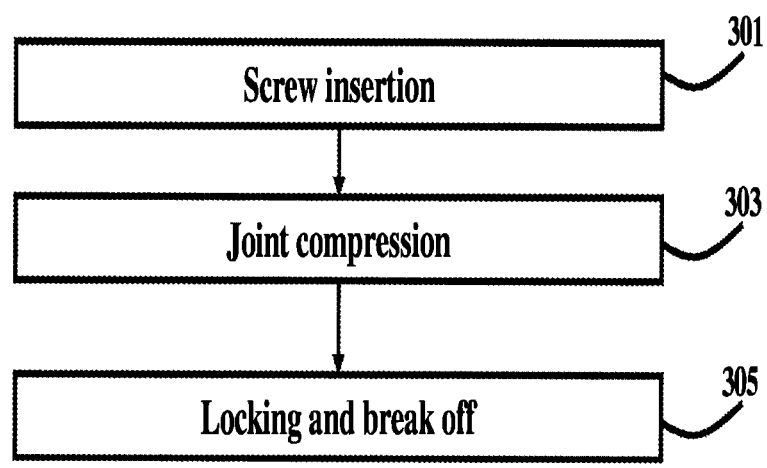
FIG. 5 is a flow diagram illustrating a method according to an embodiment herein.

FIG. 5, with reference to FIGS. 1 through 4, is a flow diagram illustrating a method according to an embodiment herein. The method includes a three step approach including a screw insertion step 301 followed by a joint compression step 303, and then followed by a locking and break off step 305.

Figure 6A:
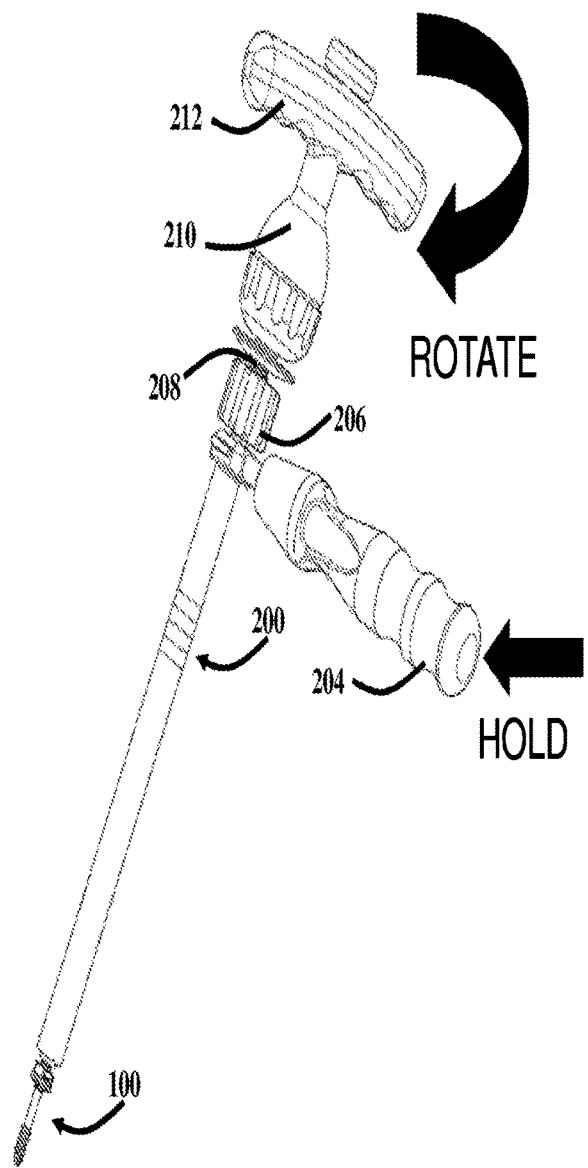
FIGS. 6A through 6C are schematic diagrams illustrating a screw insertion process according to an embodiment herein.
Figure 6B:
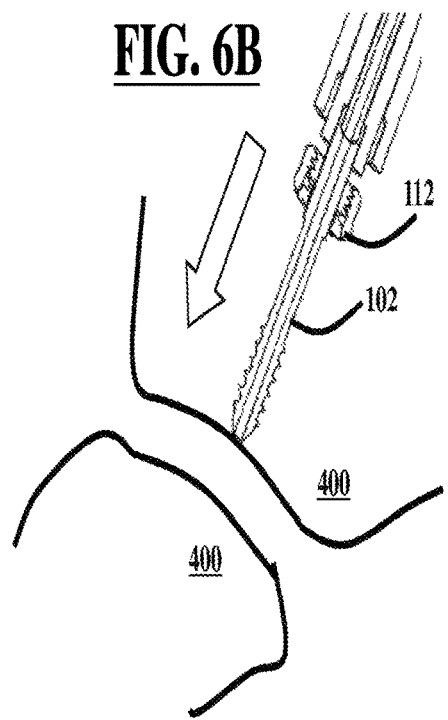
Figure 6C:
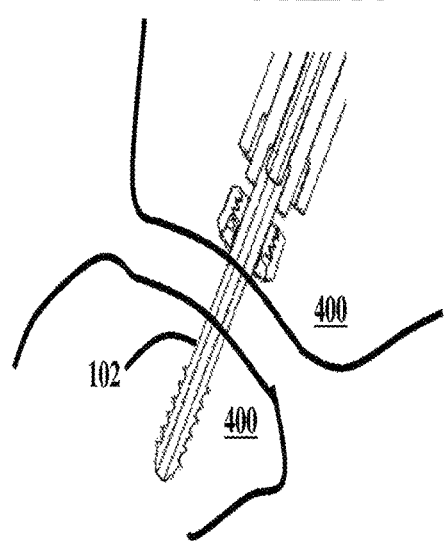

FIGS. 6A through 6C, with reference to FIGS. 1 through 5, are schematic diagrams illustrating the screw insertion process 301 according to an embodiment herein. The user (e.g., surgeon) holds the locking handle 204 and rotates the handle 210 using the arms 212 as denoted by the enlarged arrows. The rotation of the handle 210 causes the screwdriver 208 and the assembly 100 to rotate also, and the screw 102 is driven into the bone 400.

Figure 7A:
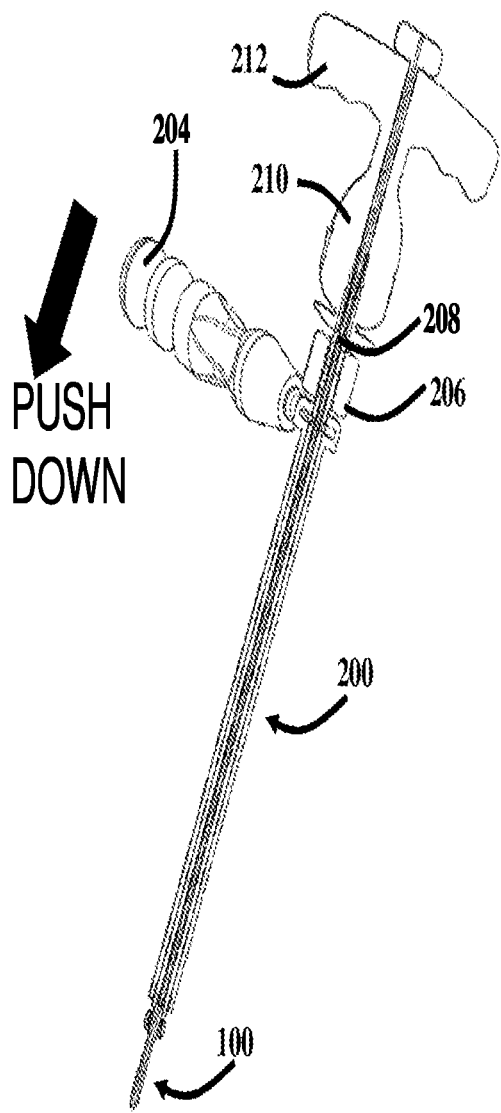
FIGS. 7A through 7C are schematic diagrams illustrating a compression process according to an embodiment herein.
Figure 7B:
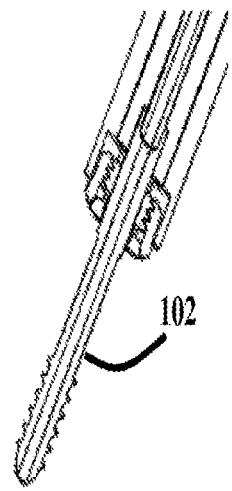
Figure 7C:
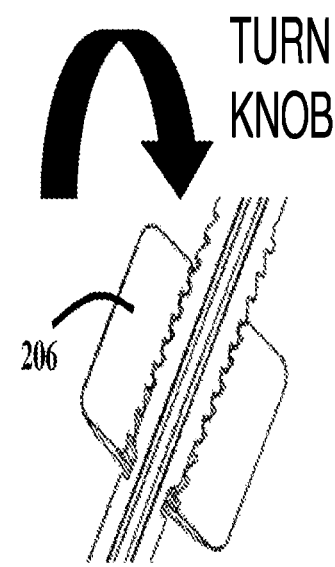

FIGS. 7A through 7C, with reference to FIGS. 1 through 6C, are schematic diagrams illustrating a compression process 303 according to an embodiment herein. First, the insertion instrument 200 is pushed down (towards the bone 400). The final locking handle assembly (e.g., shaft 202 and locking handle 204) is securely attached to the screwdriver 208. The assembly 100 is attached to the screwdriver 208 in such a way that the assembly 100 does not inadvertently slide down. However, the assembly 100 is free to rotate on the screwdriver 208. One pushes the button 207 to slide down the assembly 100 to engage the assembly 100 with the locking nut 104. After the screw 102 is inserted, the user pushes the button 207 on the locking handle 204 and slides the handle 204 down. The lower end of shaft 202 is dimensioned and configured (e.g., as an internal hex, for example) to engage the locking nut 104 (e.g., engages the outer hex walls 125 of the locking nut 104, for example) as the shaft 202 slides down. The user does not have to push down the entire instrument 200. The handle 204 is pushed down to engage the shaft 202 with the locking nut 104.

Finally, the compression knob 206 is turned. Once the final locking handle assembly (e.g., shaft 202 and locking handle 204) is engaged with the locking nut 104, the compression knob 206 is turned in order to push shaft 202 down. This process applies additional compression on the facet joint. This is why this step is called the compression step 303.

Figure 8:
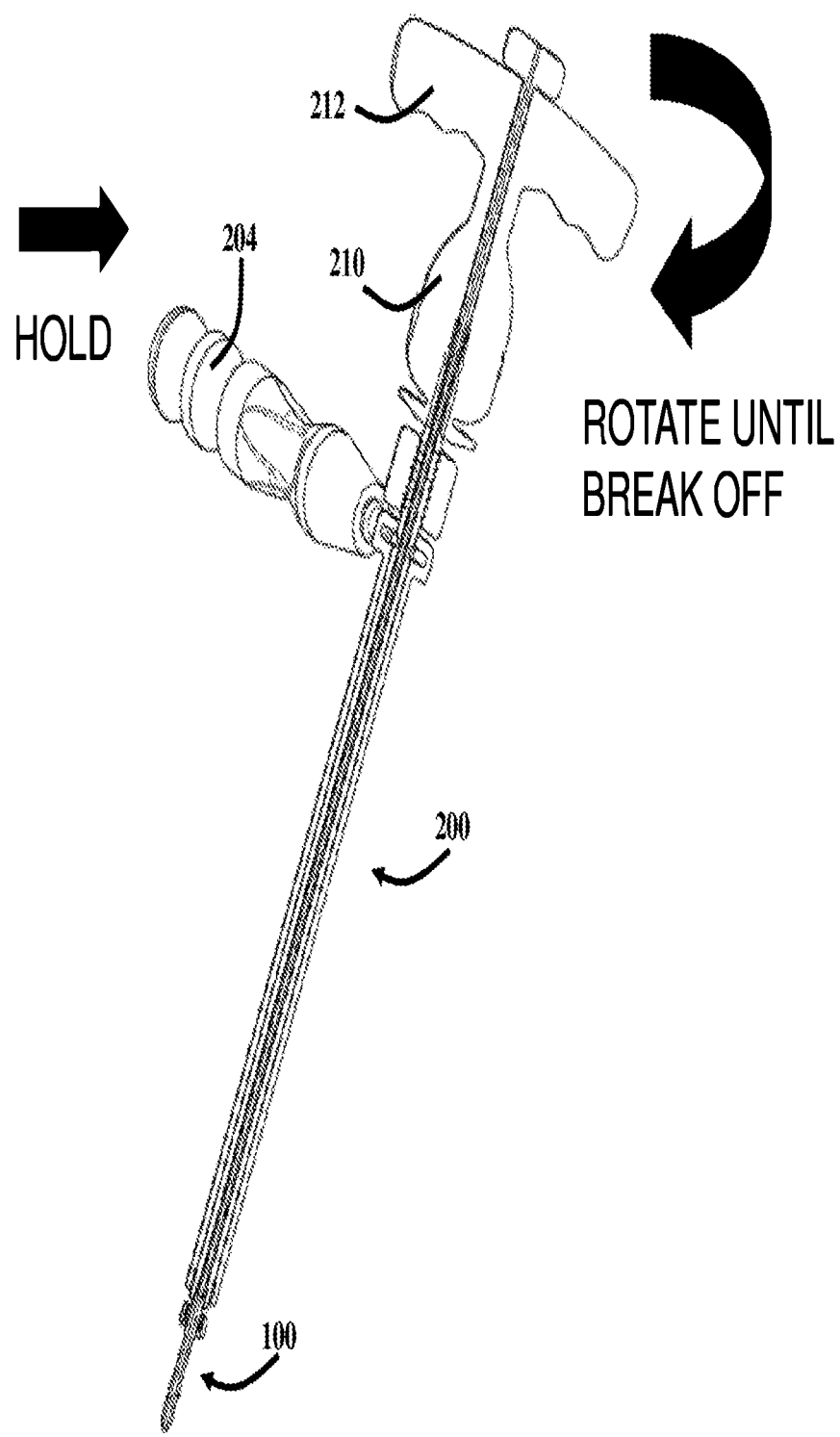
FIG. 8 is a schematic diagram illustrating a lock and break off process according to an embodiment herein.

FIG. 8, with reference to FIGS. 1 through 7C, is a schematic diagram illustrating a lock and break off process 305 according to an embodiment herein. The user holds the locking handle 204 and rotates the handle 210 until the head 122 of screw 102 breaks off. FIGS. 9A through 9C, with reference to FIGS. 1 through 8, are schematic diagrams illustrating a break off process 305 according to an embodiment herein. The assembly 100 is shown with the head 122 attached to the screw 102 in FIG. 9A. The insertion instrument 200 is attached to the implant assembly 100 before insertion. The head 122 is removed after break off occurs when the user pulls out the instrument 200. The head 122 is still attached to the instrument 200 at this point, and then may be discarded.

The collet 106 can freely translate on the neck portion 120 and head 122 (i.e., the hex regions) of the screw 102. The locking nut 104 is matingly threaded on the collet 106 (e.g., threads 108, 110). The assembly 100 is preferably pre-assembled before it is attached to the insertion instrument 200. In the assembly 100, the locking nut 104 and collet 106 are still able to translate freely prior to insertion by the insertion instrument 200. The head 122 of the screw 102 has internal threads 123 (shown in FIG. 2), which are configured to attach to the stabilizer 214 after the assembly 100 is attached to the screwdriver 208 of the insertion instrument 200. The stabilizer 214 secures the screw 102 to the screwdriver 208.

In the final step, the handle 210 is rotated to lock the collet 106 on the screw 102. This is achieved by flexing (FIG. 3C shows the collapsible nature of the collet 106) the flanges 112 of the collet 106 on the screw 102 by advancing the locking nut 104. Once a threshold torque is applied, the head 122 of the screw 102 breaks off leaving the screw assembly 100 in the patient without the unnecessary protrusion of the head 122 remaining.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A method of immobilizing a facet joint in a body, the method comprising:
   inserting a medical implant into a bone in the facet joint, wherein the medical implant comprises a bone securing component, a locking mechanism, and a holding mechanism;
   compressing the facet joint using an insertion instrument, wherein the insertion instrument comprises a shaft configured to slide to engage the locking mechanism, wherein a compression knob of the insertion instrument is turned to push the shaft in a distal direction to apply compression to the facet joint; and
   breaking off a head of the bone securing component using the insertion instrument.

2. The method of claim 1, wherein the bone securing component comprises a screw.

3. The method of claim 1, wherein the locking mechanism comprises a locking nut.

4. The method of claim 1, wherein the holding mechanism comprises a collet.

5. The method of claim 4, wherein the collet comprises a plurality of flexible flanges arranged in a substantially radial configuration.

6. The method of claim 1, wherein the step of compressing is performed after the bone securing component is fully inserted in the facet joint.

7. The method of claim 1, wherein the compression knob is turned after the shaft is engaged with the locking mechanism.

8. The method of claim 1, wherein the insertion instrument comprises a screwdriver.

9. The method of claim 1, wherein the locking mechanism and the holding mechanism are able to translate freely prior to locking the locking mechanism and the holding mechanism around the bone securing component.

10. A method of immobilizing a facet joint in a body, the method comprising:
- inserting a medical implant into a bone in the facet joint, wherein the medical implant comprises a screw, a locking nut, and a collet;
- compressing the facet joint using an insertion instrument, wherein the insertion instrument comprises a shaft configured to slide to engage the locking nut, wherein a compression knob of the insertion instrument is turned to push the shaft in a distal direction to apply compression to the facet joint; and
- breaking off a head of the screw using the insertion instrument.

11. The method of claim 10, wherein the collet comprises a plurality of flexible flanges arranged in a substantially radial configuration.

12. The method of claim 10, wherein the step of compressing is performed after the screw is fully inserted in the facet joint.

13. The method of claim 10, wherein the compression knob is turned after the shaft is engaged with the locking nut.

14. The method of claim 10, wherein the insertion instrument comprises a screwdriver.

15. The method of claim 10, wherein the locking nut and the collet are able to translate freely prior to locking the locking nut and the collet around the screw.

* * * * *